United States Patent [19]

Meyers et al.

[11] Patent Number: 5,542,921
[45] Date of Patent: Aug. 6, 1996

[54] ELECTRIC BREAST PUMP

[75] Inventors: Brenda J. Meyers; Donald W. Herritz; Jean L. Johansen, all of Reedsburg, Wis.; William B. Hudson, Jr., Fremont, Mich.; Randall P. Bell, River Forest, Ill.; Gary F. Prokop, Wheaton, Ill.; James F. Caruso, Chicago, Ill.; James l. Allen, Lake Villa, Ill.

[73] Assignee: Gerber Products Company, Fremont, Mich.

[21] Appl. No.: 334,812

[22] Filed: Nov. 4, 1994

[51] Int. Cl.$^6$ .................................................. A61M 1/06
[52] U.S. Cl. ........................... 604/74; 604/73; 604/315; 604/346
[58] Field of Search ........................ 604/73–76, 315, 604/346

[56] References Cited

U.S. PATENT DOCUMENTS 22,018  11/1858  Davidson .

(List continued on next page.)

FOREIGN PATENT DOCUMENTS

| 524638 | 3/1956 | Belgium . |
|---|---|---|
| 214394 | 3/1987 | European Pat. Off. . |
| 429086 | 9/1911 | France . |
| 1136071 | 11/1955 | France . |
| 1177525 | 6/1957 | France . |
| 1378187 | 9/1963 | France . |
| 2208875 | 9/1973 | Germany . |

(List continued on next page.)

OTHER PUBLICATIONS

Exhibit A is a copy of packaging for the "Evenflo Soft--Touch Ultra" breast pump, published by Evenflo Products Co., Ravenna, OH, copyright 1988. The product is configured for use with a battery, but includes a DC 3V jack and is thus adapted for use with an AC/DC transformer. An Adapter is provided that includes a section to support a funnel, a section to threadingly engage a bottle, and an upper end configured like a nipple.

Exhibit C is a document entitled "User's Guide—Electric Breast Pump Kit" published by Gerber, the assignee of the present application, more than one year prior to the filing of the present application, and discloses a prior ar electric breast pump.

Primary Examiner—John D. Yasko
Assistant Examiner—Laird J. Knights
Attorney, Agent, or Firm—Price, Heneveld, Cooper, DeWitt & Litton

[57] ABSTRACT

A breast pump includes a housing, a suction unit mounted in the housing, a rippled funnel for engaging a mother's breast, and an adapter for interconnecting same. The adapter is configured to sealingly support the funnel, frictionally sealingly support a bottle for collecting milk, and frictionally sealingly engage the housing. The adapter includes a tubular protrusion/stem defining a passageway for communicating air from the bottle to the suction unit to create a vacuum in the bottle. A pair of "O" rings are positioned on the protrusion to sealingly and stably engage the housing. A check valve is located in the protrusion to prevent back flow of milk from the bottle to the suction unit. The housing includes an outer surface defining a hand grip, and vacuum adjustment controls including a wheel for fine vacuum adjustment and a vacuum releasing push bottom are conveniently positioned on the hand grip. The housing includes a shroud that protects the bottle and that forms a stable arrangement that the entire unit will stand upright on a table. The shroud defines a battery holder and further includes a jack for mateably engaging an AC/DC transformer outlet for optional operation of the motor in lieu of batteries. The hand grip and the battery placement provide an optimal center of gravity located below the hand grip so that the breast pump can be easily, comfortably and securely held. The funnel includes three ring-shaped undulations providing increased comfort, size adaption and functionality to the funnel.

43 Claims, 9 Drawing Sheets

U.S. PATENT DOCUMENTS

| | | |
|---|---|---|
| D. 251,015 | 2/1979 | Cone . |
| D. 283,732 | 5/1986 | Elliott . |
| D. 299,537 | 1/1989 | Morifuji . |
| D. 307,478 | 4/1990 | Morifuji . |
| D. 309,500 | 7/1990 | Yuan et al. . |
| D. 313,103 | 12/1990 | Kawano . |
| D. 326,319 | 5/1992 | Chambers . |
| D. 326,516 | 5/1992 | Chambers . |
| D. 345,209 | 3/1994 | Shoda et al. . |
| D. 348,513 | 7/1994 | Bale . |
| 361,910 | 4/1887 | Tutton . |
| 420,195 | 1/1890 | Graves et al. . |
| 684,078 | 10/1901 | Martin . |
| 1,624,254 | 4/1927 | Kostenko et al. . |
| 1,992,491 | 2/1935 | Lindsay . |
| 2,109,718 | 3/1938 | Bayers . |
| 2,162,076 | 6/1939 | Frimand . |
| 2,222,811 | 11/1940 | Von Grolman . |
| 2,419,795 | 4/1947 | Saunders . |
| 2,559,067 | 7/1951 | Doeg . |
| 2,575,398 | 9/1954 | Schroeder . |
| 2,690,295 | 9/1954 | Rand . |
| 3,699,815 | 10/1972 | Holbrook . |
| 3,738,363 | 6/1973 | Lunas et al. . |
| 3,782,385 | 1/1974 | Loyd . |
| 3,822,703 | 7/1974 | Davisson . |
| 3,825,374 | 7/1974 | Kondo . |
| 4,263,912 | 4/1981 | Adams . |
| 4,419,093 | 12/1983 | Deaton . |
| 4,583,970 | 4/1986 | Kirchner . |
| 4,673,388 | 6/1987 | Schlensog et al. .................... 604/74 |
| 4,680,028 | 7/1987 | Stuart . |
| 4,754,776 | 7/1988 | McKee . |
| 4,759,747 | 7/1988 | Aida et al. . |
| 4,761,160 | 8/1988 | Vermillion . |
| 4,772,262 | 9/1988 | Grant et al. . |
| 4,774,874 | 10/1988 | Adahan . |
| 4,799,922 | 1/1989 | Beer et al. . |
| 4,813,932 | 3/1989 | Hobbs ........................ 604/64 |
| 4,883,464 | 11/1989 | Morifuki ..................... 604/74 |
| 4,886,494 | 12/1989 | Morifuji ..................... 604/74 |
| 4,892,517 | 1/1990 | Yuan et al. . |
| 4,929,229 | 5/1990 | Larsson . |
| 4,950,236 | 8/1990 | Wilson . |
| 4,961,726 | 10/1990 | Richter . |
| 4,964,851 | 10/1990 | Larsson ..................... 604/74 |
| 5,007,899 | 4/1991 | Larsson . |
| 5,009,638 | 4/1991 | Riedweg et al. . |
| 5,049,126 | 9/1991 | Larsson ..................... 604/74 |
| 5,071,403 | 12/1991 | Larsson . |
| 5,100,406 | 3/1992 | Panchula ................... 604/74 |
| 5,295,957 | 3/1994 | Aida et al. . |
| 5,308,321 | 5/1994 | Castro . |

FOREIGN PATENT DOCUMENTS

| | | |
|---|---|---|
| 2439964 | 9/1975 | Germany . |
| 3605083 | 8/1987 | Germany . |
| 3721952 | 2/1988 | Germany . |
| 407293 | 11/1949 | Italy . |
| 54-44213 | 4/1979 | Japan . |
| 59-200081 | 11/1984 | Japan . |
| 59-200083 | 11/1984 | Japan . |
| 158976 | 5/1957 | Sweden . |
| 762701 | 12/1956 | United Kingdom . |
| 2082920 | 3/1982 | United Kingdom . |
| 2127293 | 4/1984 | United Kingdom . |
| 2155792 | 10/1985 | United Kingdom . |
| WO9011097 | 10/1990 | WIPO . |

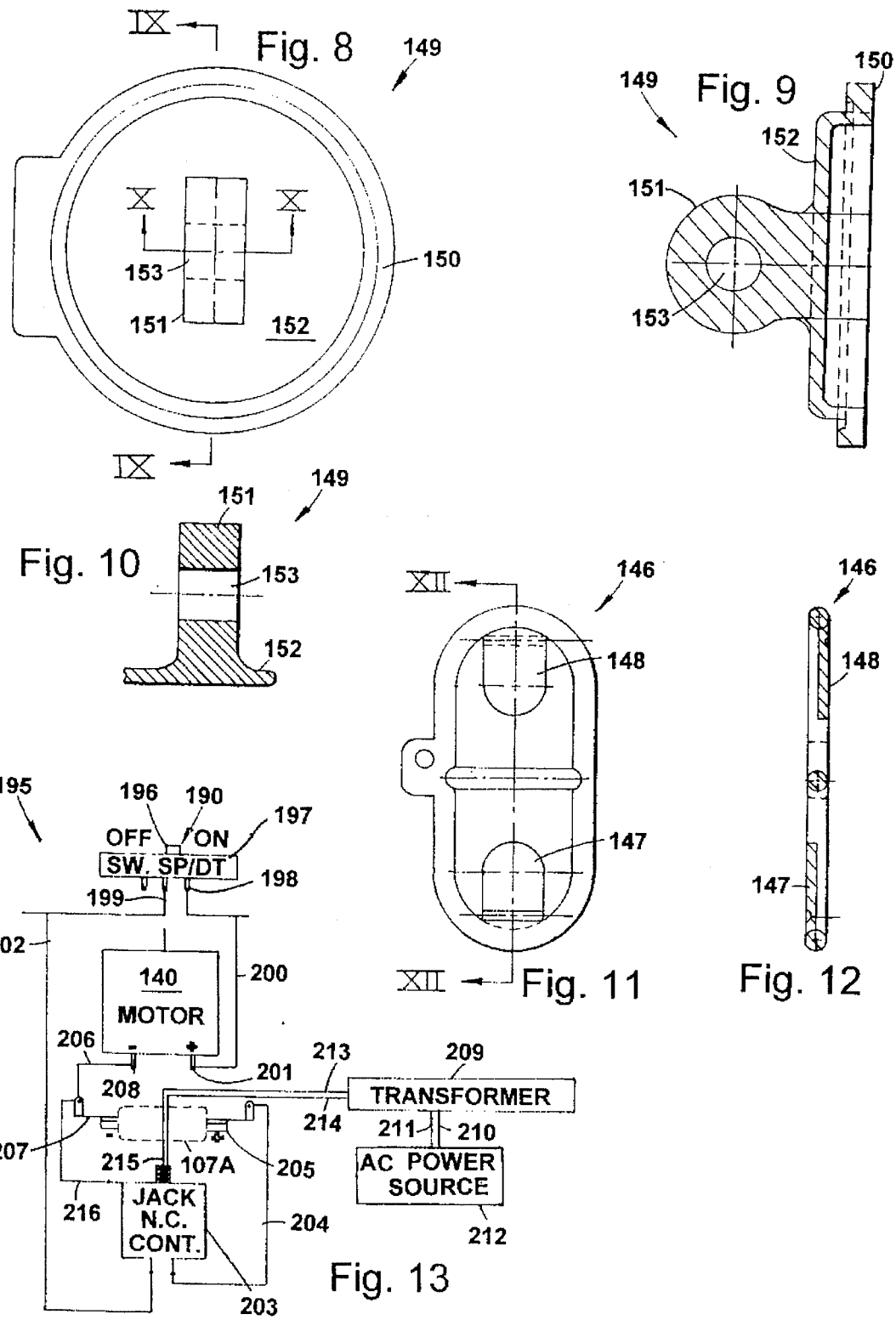

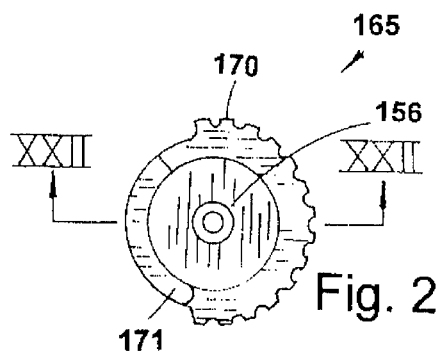
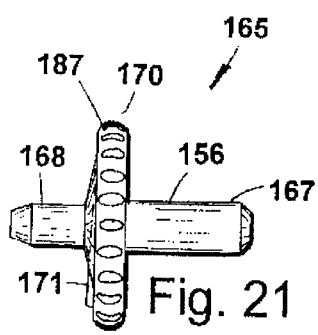
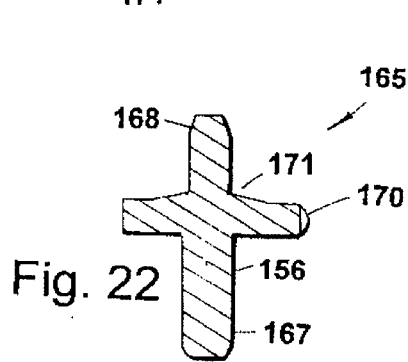
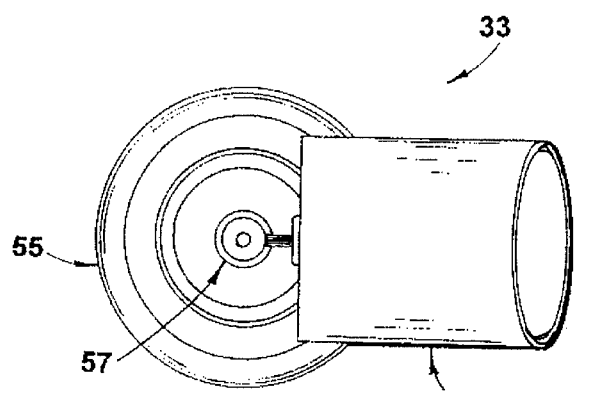
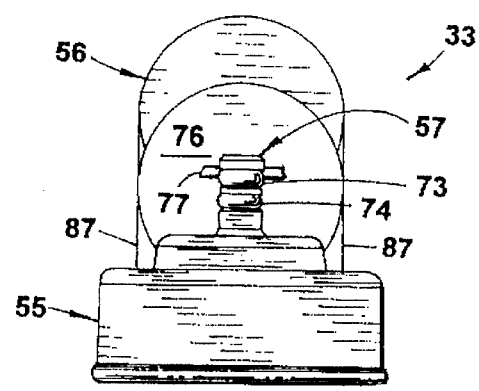
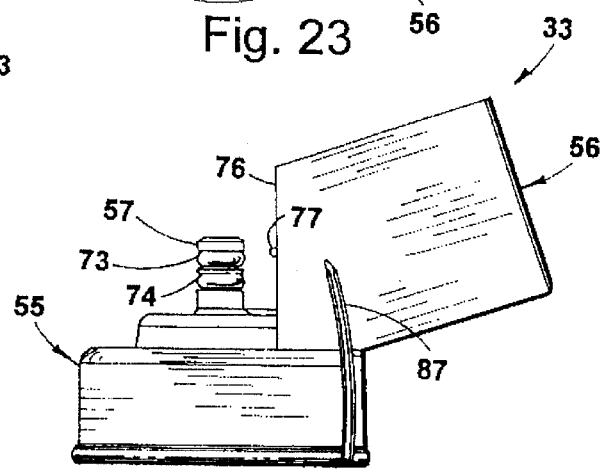
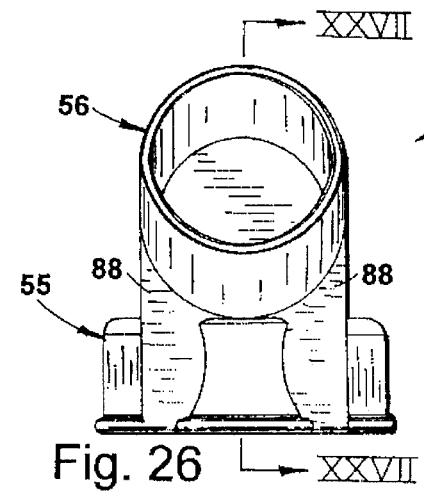
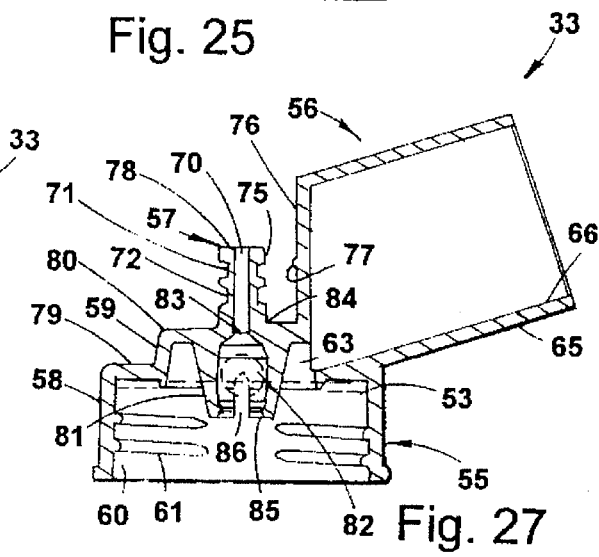

ELECTRIC BREAST PUMP

BACKGROUND OF THE INVENTION

The present invention concerns breast pumps for extracting and collecting milk from a mother's breast, and more particularly concerns an electrically operated breast pump configured for comfortable, convenient, and safe use, as well as for easy cleaning and improved function.

In breast pumps, it is very important that the device be comfortable to use and operate so that the process of extracting milk is as frustration-free and natural as possible. Typically, a constant vacuum adjustment control and a vacuum pulsing control are provided. However, many of these vacuum controls on breast pumps are not located for convenient manipulation while using the breast pump. Thus, either the mother must interrupt her use of the breast pump to adjust the vacuum or must at least use two hands and/or also look at the breast pump to operate the controls.

Another problem is that many known breast pumps are large and/or bulky. Not only do they take up "too much" space, but large breast pumps tend to be awkward to operate. Recently, breast pumps have been designed that are more compact. However, many of the compact breast pumps are top-heavy and unbalanced. Top-heavy and unbalanced breast pumps can be uncomfortable to use. Also, they are often not stable when rested on a flat surface such as a table or countertop. For example, unstable breast pumps tend to tip over when rested on a flat surface, causing milk to wash against the suction unit on the breast pump. This can cause a sanitation problem and further can cause mechanical/functional problems, such as when milk enters and clogs the suction pump of the breast pump. The tendency of a breast pump to tip over also can be very frustrating to a mother.

Yet another problem is the difficult disassemble/assembly required by many breast pumps. In particular, those breast pumps that are securely interconnected as a unit tend to require a cumbersome disassembly in order to properly clean and sanitize all parts. Contrastingly, those breast pumps that are easy to disassemble are not as securely interconnected as desired. Thus, a stable attachment mechanism is desired that provides quick disassembly, secure interconnection and which is sanitary and easy to clean.

Another problem with many breast pumps is that their funnels are not adapted to sealingly engage the shapes and sizes of different mother's breasts. Merely providing at a large diameter funnel is not an adequate solution since the funnel must flex and resiliently bend to receive a mother's nipple and breast without losing the sealing engagement that allows the vacuum to be drawn. Some funnels have been designed with undulated or curved sidewalls, however, further improvement is desired to control the flexing of the funnel wall so that the desired flexing occurs without concurrent loss of comfort or functionality.

Thus, a breast pump solving the aforementioned problems is desired, including the ability to satisfy the preferences and physical needs of different mothers.

SUMMARY OF THE INVENTION

In one aspect, the present invention includes a breast pump having a housing, and a suction unit operably mounted to the housing, with one of the housing and the suction unit defining a suction inlet. An adapter includes a tubular protrusion configured to engage the suction inlet, a funnel-supporting section for supporting a funnel to engage a mother's breast and a bottle engaging section for holding a bottle to collect milk extracted from the mother's breast. A pair of spaced "O" rings engage the tubular protrusion and the suction inlet for creating a substantially air tight and stable seal between the tubular protrusion and the suction inlet. The "O" rings also frictionally engage the suction inlet to retain the adapter to the housing.

In another aspect, the present invention includes a breast pump having a funnel for mateably engaging a mother's breast, a suction unit for withdrawing air from the funnel to create a vacuum therein, and a housing assembly configured to support the funnel and the suction unit. The housing assembly includes a housing defining a hand grip having a thumb position located generally on the same side of the housing as the funnel, and controls for controlling the suction unit located on the hand grip in the thumb position.

In another aspect, the present invention includes a hand held portable breast pump having a vacuum-generating unit configured to mateably engage a mother's breast and to extract milk therefrom for collection in a container. The vacuum-generating unit includes a housing having contoured surfaces defining a hand grip with depressions therein shaped to mateably receive a mother's hand such that the hand grip is substantially "slip free" and a suction unit operably mounted in the housing. A vacuum control mechanism is located in the housing and operably connected to the suction unit. The vacuum control mechanism includes a valve for controlling the vacuum generated by the suction unit, a rotatable thumb wheel operably connected to the valve for controlling fine adjustment of the vacuum, and a push button operably connected to the valve and spaced from the thumb wheel for venting the suction unit to atmosphere. The thumb wheel and the push button are operably mounted to the housing and are located on the hand grip for convenient operation by a thumb or a finger on the mother's hand while she is holding onto the hand grip.

In yet another aspect, a breast pump includes a portable hand held vacuum-generating unit configured to mateably engage a mother's breast and to extract milk therefrom for collection in a bottle. The vacuum-generating unit includes a bottle-engaging section and shroud. The shroud has a bottom surface spaced a predetermined distance from the bottle-engaging section such that the shroud bottom surface is generally co-planar with a bottom surface of the bottle when the bottle is engaged with the bottle-engaging section. Thus, when the bottle is assembled to the breast pump, the shroud bottom surface combines with the bottle bottom surface to stably support the breast pump and the bottle in an upright position.

In anther aspect, the present invention includes a hand held portable breast pump including a housing having an upper section with a contoured surface defining a hand grip and a suction inlet, and further having a lower section defining a shroud with a concave generally arcuate surface for mateably partially surrounding and protecting a bottle. A suction unit is operably mounted in the housing and connected to the suction inlet. A funnel is provided configured to mateably engage a mother's breast, and an adapter operably interconnects the funnel in the housing. The adapter is configured to operably engage a bottle and position the bottle in a protected position adjacent the arcuate surface of the shroud.

In another aspect, the present invention includes a self-supporting funnel for a breast pump having a generally cylindrically-shaped tubular section comprising resilient material and a generally frustoconically-shaped funnel section also comprising resilient material. The tubular section has a constant wall thickness and is configured to mateably engage a breast pump for delivering milk to a container attached to the breast pump. The funnel section defines a constant thickness wall with at least three circumferentially extending ring-shaped undulations that cause the wall to flex in a symmetrical manner to comfortably and sealingly engage a mother's breast despite physical differences in size and shape of breasts of one mother to another.

The preferred embodiment of the breast pump disclosed herein advantageously provides a housing that defines a hand grip having a vacuum adjustment control and a vacuum pulsing control in the thumb position of the hand grip. This makes the breast pump relatively easy to use, and in particular, allows a mother to both control and use the breast pump with one hand. Thus, the mother's second hand is free to attend to other matters, such as her infant. Further, the breast pump is configured to stably rest on a flat surface, such that it can be conveniently set on a table or countertop without fear of tipping over. The shroud contributes to the stability of the breast pump by providing a flat bottom surface that aligns with the flat surface on a bottle attached to the breast pump. The shroud also provides a battery holder that is positioned low on the breast pump, thus contributing to a low center of gravity. Still further, the shroud protects the bottle on the breast pump. An adapter includes a stem and spaced "O" rings on the stem for securely retaining an assembly of the bottle/funnel/adapter to the housing of the breast pump. The "O" rings provide a sanitary connection that is secure, but which is conveniently releasible with a gentle but firm pull for easy cleaning. Also, the funnel is rippled with circumferentially-extending undulations so that it can mateably engage a variety of shapes and sizes of mothers' breasts without loss of comfort or functionality.

BRIEF DESCRIPTION OF THE DRAWINGS

FIG. 8 is a plan view of the flexible member of the pump shown in FIG. 7;

FIG. 9 is a cross-sectional view taken along the lines IX—IX in FIG. 8;

FIG. 10 is a fragmentary cross-sectional view taken along the lines X—X in FIG. 8;

FIG. 11 is a plan view of the valve of the vacuum pump shown in FIG. 6;

FIG. 12 is a cross-sectional view taken along the line XII—XII in FIG. 11;

FIG. 13 is an electrical schematic showing the circuitry for connecting the motor to a power source;

FIG. 20 is an end view of the valve rod for controlling the vacuum pressure in the suction unit;

FIG. 21 is a side view of the valve rod shown in FIG. 20;

FIG. 22 is a cross-sectional view taken along the lines XXII—XXII in FIG. 20;

FIG. 23 is a top view of the adapter shown in FIG. 5;

FIG. 24 is a rear view of the adapter shown in FIG. 23;

FIG. 25 is a side view of the adapter shown in FIG. 23;

FIG. 26 is a side view of the adapter shown in FIG. 23; and

FIG. 27 is a cross-sectional view taken along the lines XXVII—XXVII in FIG. 26.

DETAILED DESCRIPTION OF PREFERRED EMBODIMENT

Figure 1:
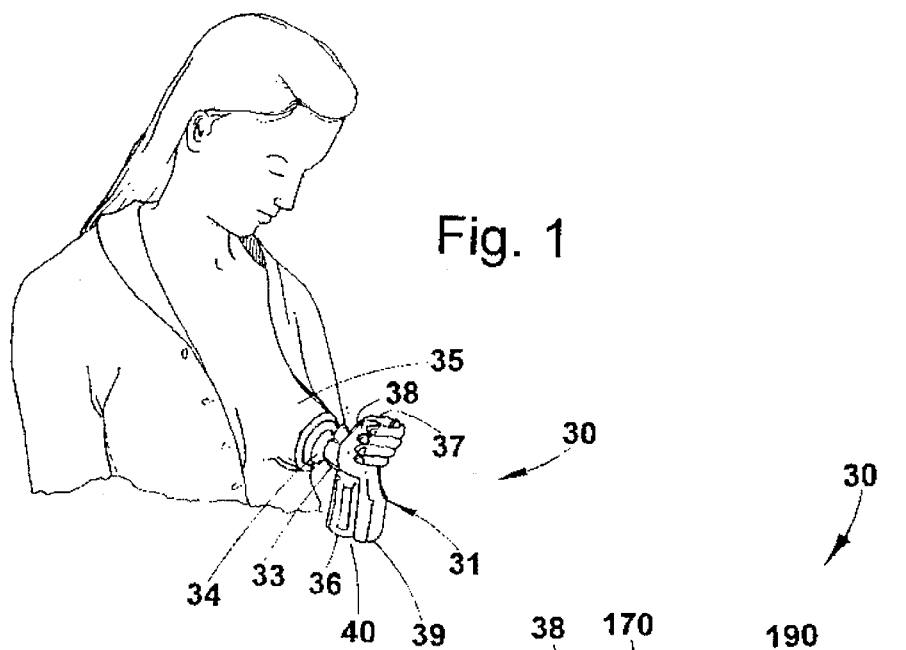
FIG. 1 is a perspective view of a mother using a breast pump embodying the present invention.
Figure 2:
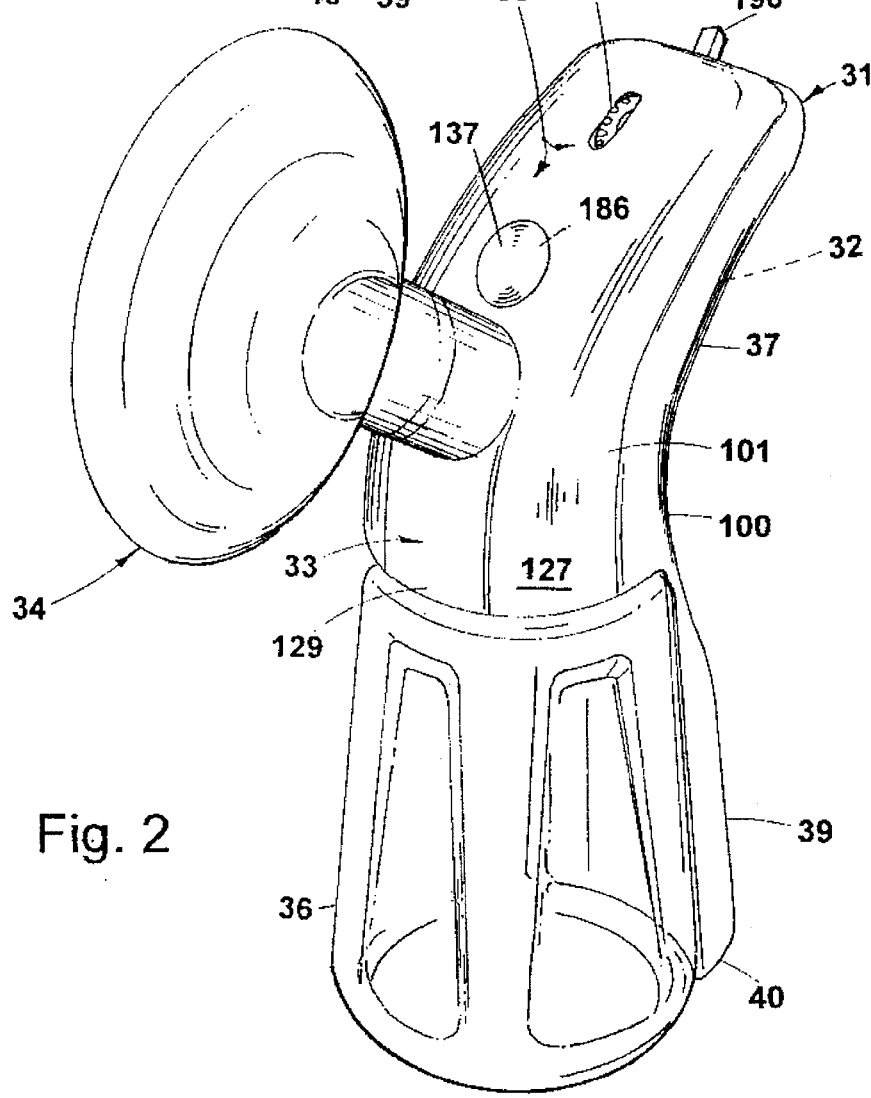
FIG. 2 is a perspective view of the breast pump shown in FIG. 1.
Figures 3, 4:
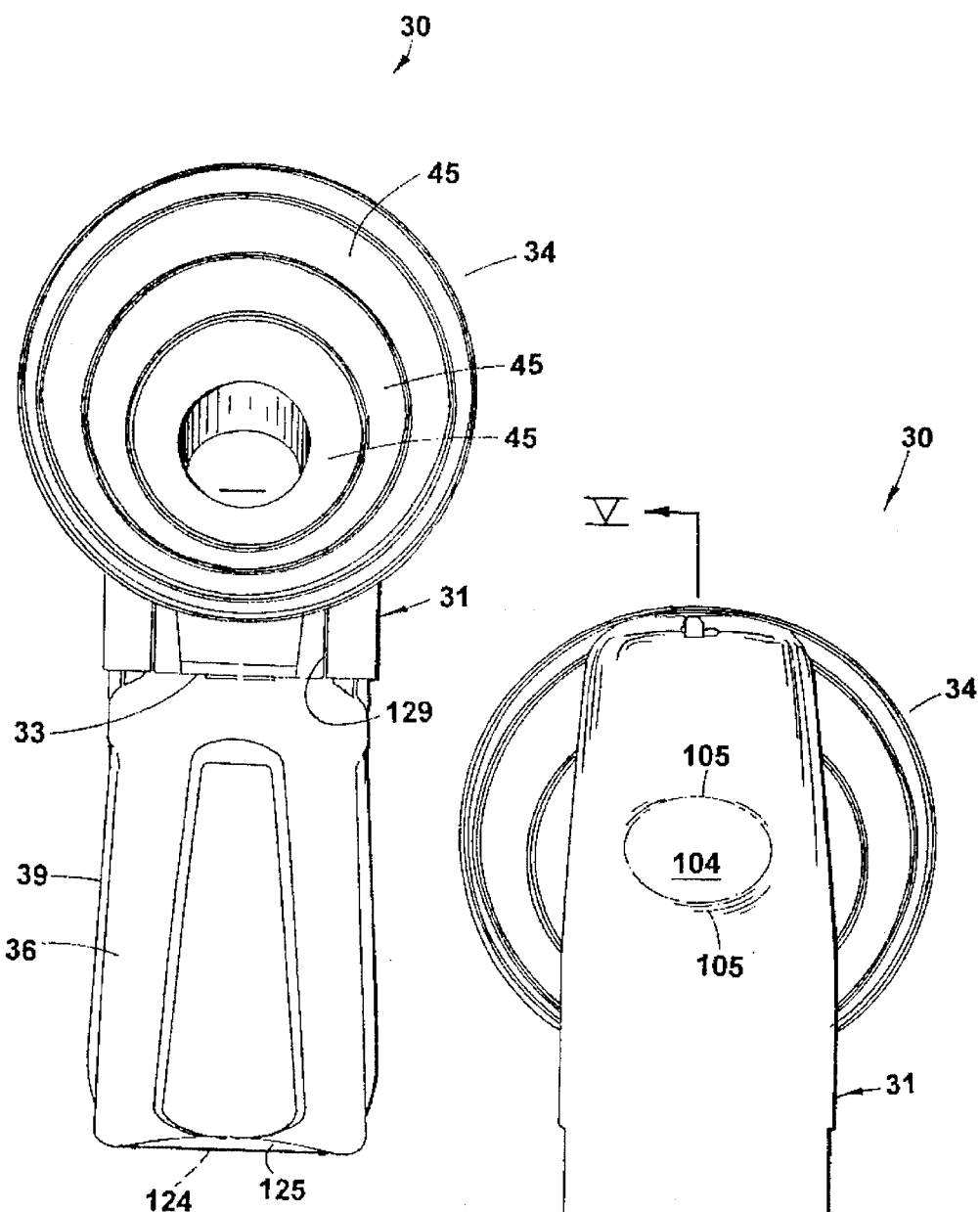
FIG. 3 is a front view of the breast pump shown in FIG. 2.
FIG. 4 is a rear view of the breast pump shown in FIG. 2.
Figure 6:
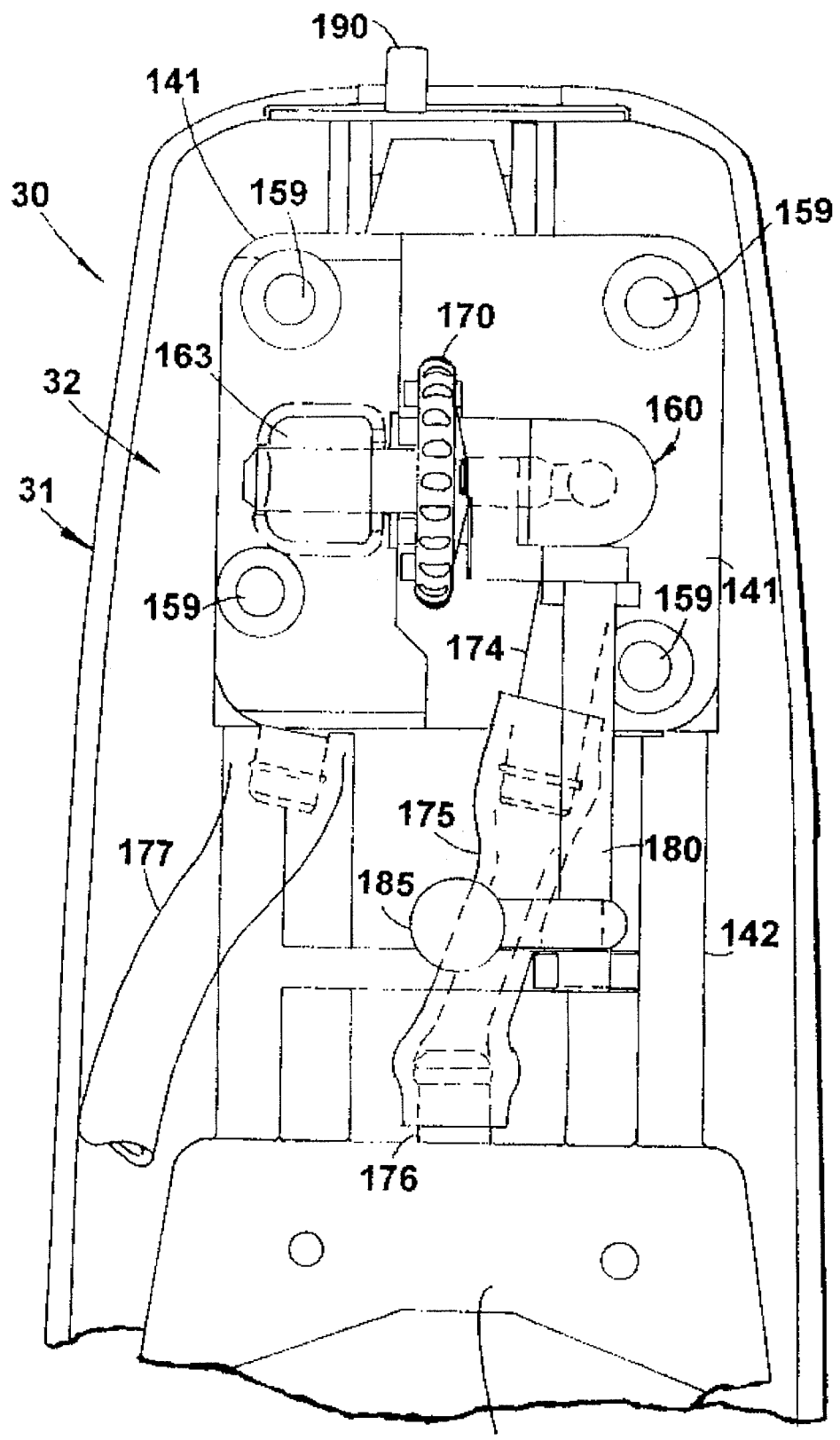
FIG. 6 is a plan view of the suction unit shown in FIGS. 5 and 5A.

For purposes of description herein, the terms "upper," "lower", "right," "left," "front," "rear," "vertical," "horizonal" and derivatives thereof shall relate to the invention as oriented in FIG. 1, the breast-engaging funnel being at the "front" of the device, and the "right side" of the device being on the mother's right side. However, it is to be understood that the invention may assume various alternative orientations, except where expressly specified to the contrary. It is also to be understood that these specific devices and processes illustrated in the attached drawings, and described in the following specification are simply exemplary embodiments of the inventive concepts defined in the appended claims. Hence, specific dimensions and other physical characteristics that relate to the embodiments disclosed herein are not to be considered as limiting unless the claims expressly state otherwise.

A breast pump 30 (FIGS. 1–2) embodying the present invention includes a housing 31, a suction unit 32 operably mounted in the housing 31 (FIGS. 5, 5A, 6–12, and 14–22), an adapter 33 frictionally operably secured to the housing 31 (FIGS. 23–27), and a funnel 34 engaged with the adapter 33 (FIGS. 1–5). The suction unit 32 is configured to withdraw air from the funnel 34 to create a vacuum that extracts milk from the mother's breast 35, which milk flows through the funnel 34 and the adapter 33 into a bottle 36 secured to the adapter 33. Breast pump 30 is configured to provide comfortable and safe operation despite differences in physical needs and preferences between mothers. For example, the housing 31 includes a hand grip 37 and controls 38 on the same side of the hand grip 37 on which funnel 34 is positioned enabling one-handed operation of the breast pump 30, and further includes a shroud 39 having a lower end 40 positioned such that it forms a stable support for the breast pump 30 to hold the breast pump in an upright position when rested on a table surface, regardless of whether bottle 36 is filled or empty. Further, the breast pump 30 can be easily disassembled for cleaning without the need for separate tools.

More specifically, funnel 34 (FIG. 5) includes a generally cylindrically-shaped tubular section 43, and a generally frustoconically-shaped funnel section 44. Funnel 34 is made of material that can be readily deformed and flexed, but which is resilient and self-supporting, such as silicon rubber. The tubular section 43 has a constant wall thickness and is configured to mateably and sealingly engage the interior of adapter 33 for delivering milk to a container or bottle 36 attached to breast pump 30. Funnel section 44 also defines a constant wall thickness having a thickness dimension slightly less than tubular section 43 such that funnel section 44 is somewhat more flexible than tubular section 43. However, funnel section 44 is still sufficiently stiff to be self-supporting. Funnel section 44 includes three circumferentially extending ring-shaped undulations 45 configured to securely and comfortably, sealingly engage a mother's breast 35. The undulations or ripples 45 extend circumferentially around funnel 44 and are arcuately-shaped. The undulations 45 each have substantially an identical cross-sectional shape in the "longitudinal" direction. Further, the three undulations 45 take up the entire length of funnel section 44.

Funnel section 44 defines an inner surface 46 and an outer surface 47. The funnel section 44 defines a plurality of tangential lines such as lines 45' that tangentially touch the innermost points of inner surface 46 on undulations 45. Tangential lines 45' extend through central axis 45" of funnel section 44. The depth "D1" of undulations 45 relative to the tangential lines 45' is about equal to the thickness of the wall of funnel section 44. This shallow depth and the resiliency of the funnel material causes the funnel section 44 to flex in a symmetrical, controlled manner to comfortably and sealingly engage a mother's breast without losing its sealing engagement with the breast. In addition, the concentric undulations enable funnel 34 to tightly and sealingly fit successively smaller or larger breast sizes without requiring a change in funnels.

Adapter 33 (FIGS. 5 and 23–27) includes a cup-shaped section 55, a funnel-supporting section 56 extending from bottle-engaging cup-shaped section 55, and a tubular protrusion or stem 57 also extending from cup-shaped section 55. Cup-shaped section 55 (FIG. 27) includes a cylindrically-shaped side wall 58 and a top wall 59 connected to side wall 58. The inner surface 60 of side wall 58 includes threads 61 configured to receive a ring-shaped gasket or seal 53 for sealingly engaging the mouth or upper lip 62 of bottle 36. A passageway 63 is defined through funnel-supporting section 56 and top wall 59. Funnel-supporting section 56 includes a tubular section 65 having a substantially constant diameter, cylindrically-shaped inner surface 66 with a diameter chosen to sealingly matingly engage the outer surface of tubular section 43 (FIG. 5) on funnel 34. Thus, the inner space 67 in bottle 36 is placed in fluid communication with the inner space 66 defined within funnel-supporting section 56 of funnel 34.

Protrusion or stem 57 of adapter 33 (FIG. 27) extends vertically upwardly from the center of top wall 59 and defines a passageway 70 that extends through tubular protrusion 57 and top wall 59. Tubular protrusion 57 includes annular ring-shaped depressions 71 and 72 that are spaced from top wall 59 and spaced from each other. "O" rings 73 and 74 (FIGS. 24–25) are positioned in depressions 71 and 72 (FIG. 27) and extend slightly outwardly from the outer surface 75 of protrusion or stem 57. The inner end of funnel-supporting section 56 defines a planar vertical surface 76 spaced from and lying parallel to protrusion 57. A horizontally extending ridge 77 is located about midway on surface 76 such that it is located vertically lower than the end 78 of protrusion 57. Top wall 59 includes an outer ring 79 that engages the top of bottle 36, and further includes a centrally located raised section 80 that supports protrusion 57. On the underside of raised section 80 is a tubular protrusion 81 having a ball 82 loosely held therein. The opening 83 defined at the base of tubular protrusion 57 includes a chamfered surface or seat 84 configured to mateably receive ball 82 such that ball 82 acts as a check valve to prevent back flow of milk from bottle 36 through passageway 70 into suction unit 32, such as may happen when breast pump 30 is rested on its side and milk flows from within bottle 36 against adapter 33. Notably, ball 82 has enough weight to prevent it from being sucked against seat 84 during normal "vertical" operation of breast pump 30, but is light enough to float in milk such that ball 82 will immediately seal against seat 84 if the bottle 36 becomes full with milk or if breast pump 30 is laid on its side and milk washes against a suction inlet 92, as discussed hereinafter. Preferably, ball 82 is made from a polymeric material such as polypropylene having a specific gravity of about 0.90 and a total weight of about 0.16 grams.

The lower end of "check valve" tubular protrusion 81 includes inwardly facing lips 85 configured to retain ball 82 within tubular protrusion 81, and further includes vertically extending slots 86 for allowing air from bottle 36 to pass around ball 82 into tubular protrusion 81 and thus into passageway 70 of tubular protrusion 57. Reinforcement ribs 87 (FIGS. 24–25) extend from the sides of funnel-supporting section 56 downwardly onto side wall 58 to support and rigidify funnel-supporting section 56 to bottle-engaging section 55, and to form an exterior surface 88 which mates with opening 129 of housing 31 to close the opening therein when adapter 33 is installed as is more fully explained below.

Figure 5:
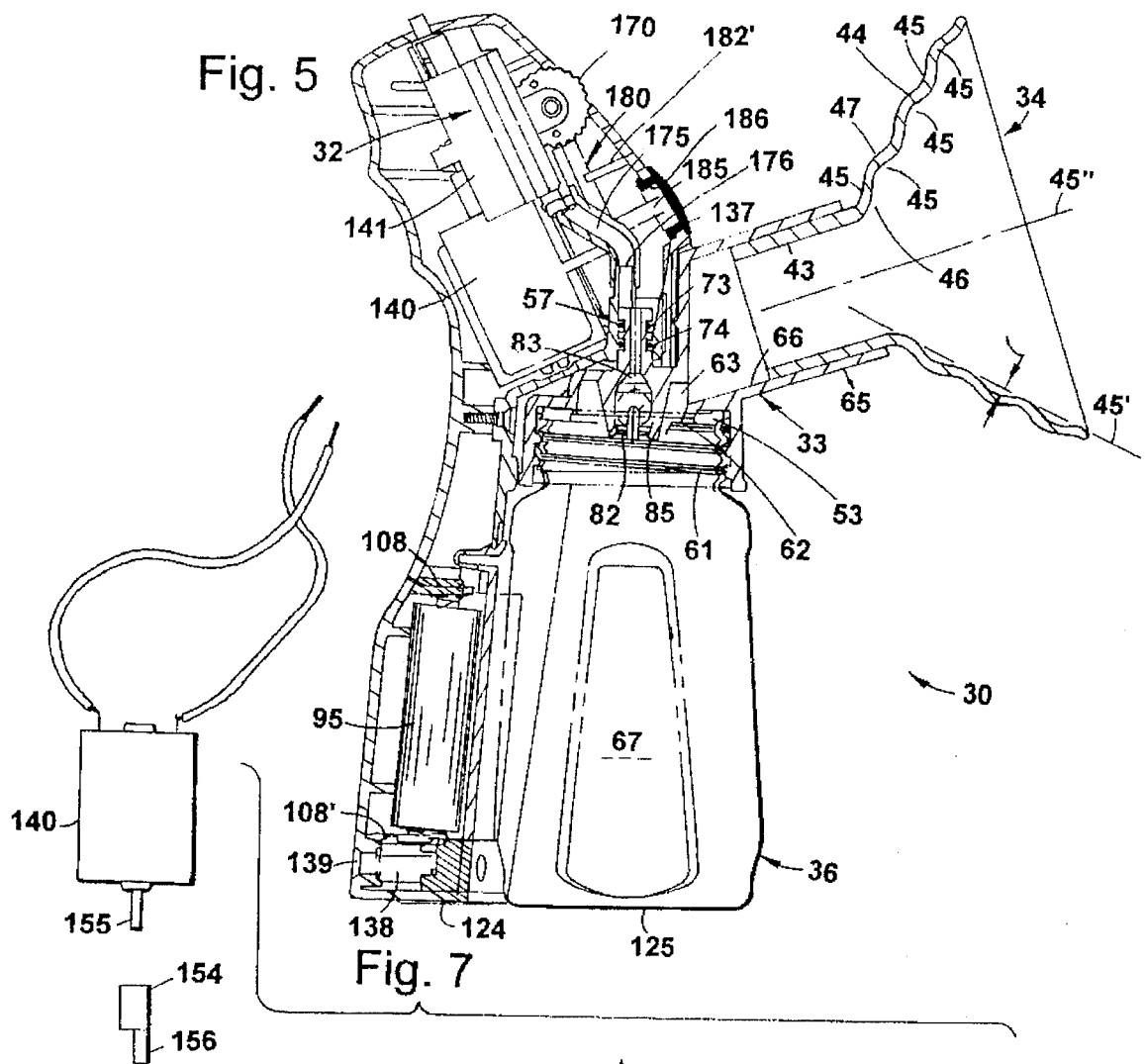
FIG. 5 is a cross-sectional view taken along the lines V—V in FIG. 4.
Figure 7:
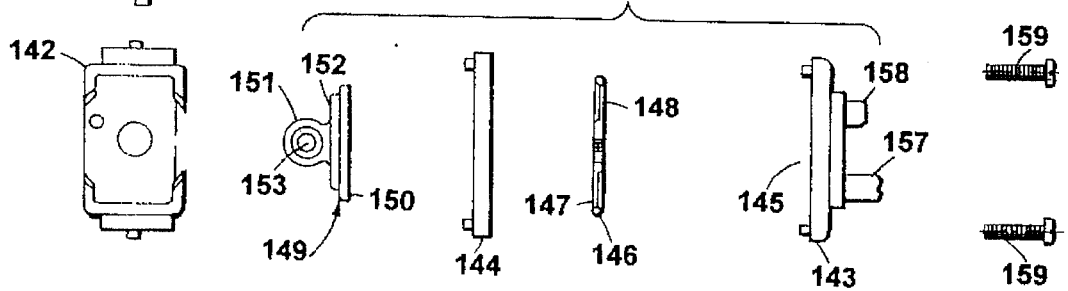
FIG. 7 is an exploded side view of the motor and vacuum pump.
Figure 5A:
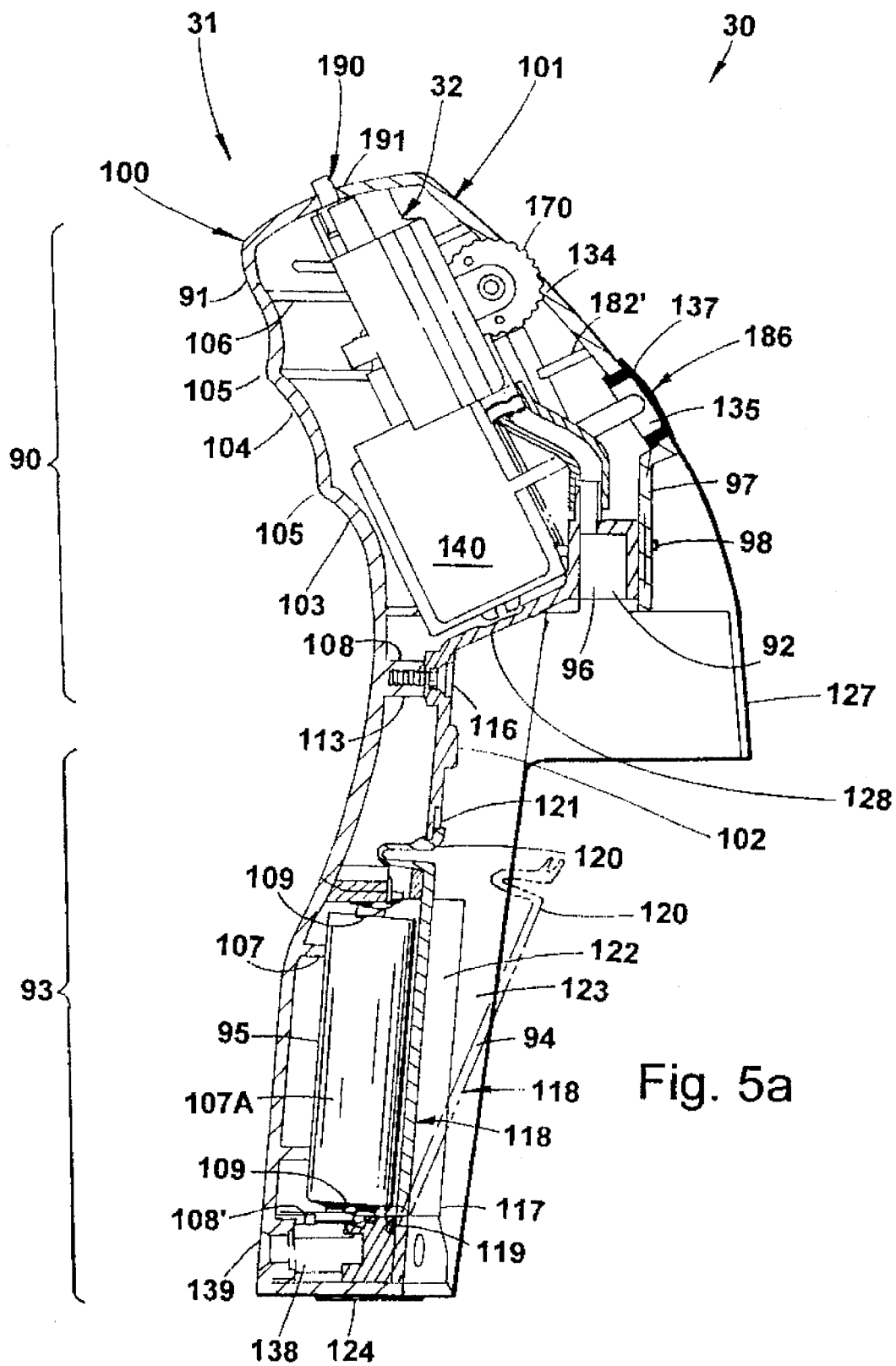
FIG. 5A is a cross-sectional view of the housing and suction unit shown in FIG. 5.
Figure 16:
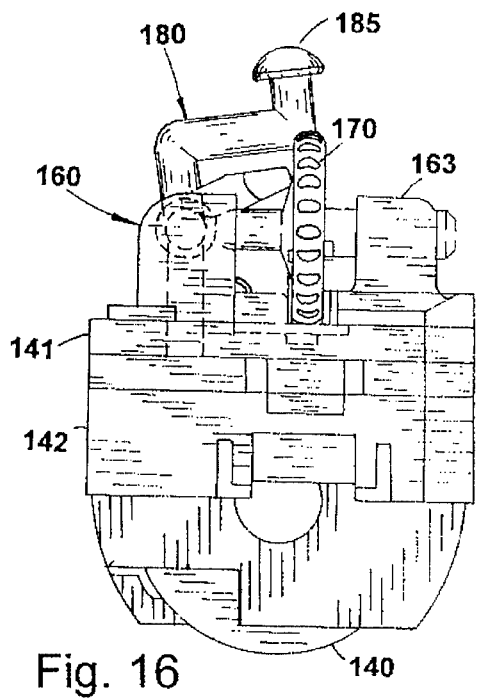
FIG. 16 is a top view of the suction unit shown in FIG. 14.
Figure 17:
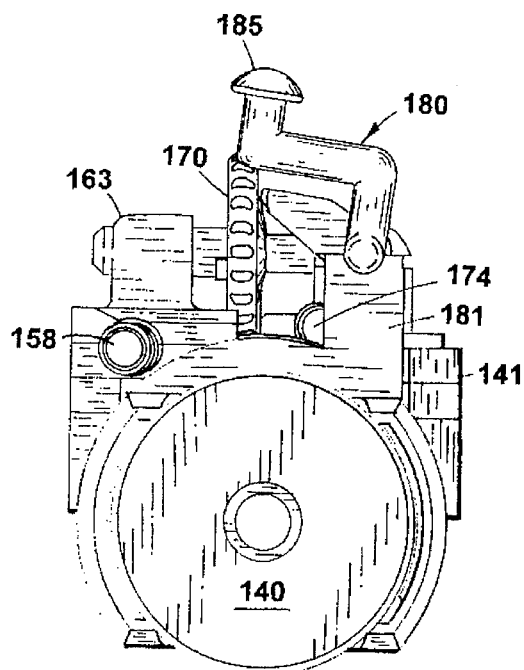
FIG. 17 is a bottom view of the suction unit shown in FIG. 14.
Figure 14:
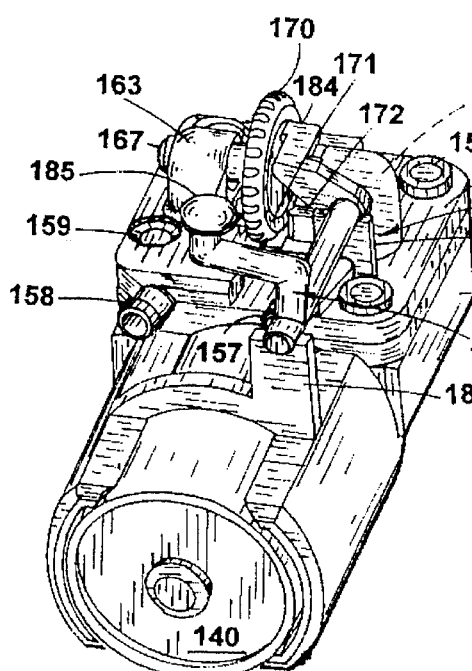
FIG. 14 is a bottom front perspective view of the suction unit shown in FIG. 5.

Housing 31 (FIG. 5A) includes an upper section 90 having a contoured surface 91 defining a hand grip and a suction inlet 92, and further includes a lower section 93 defining a shroud 94 and a battery holder 95. Suction inlet 92 includes a cylindrically-shaped smooth surface 96 having a diameter chosen to sealingly frictionally engage "O" rings 73 and 74 (FIGS. 5A and 24). Notably, the spacing of "O" rings 73 and 74 creates a stable engagement of stem or protrusion 57 with cylindrically-shaped surface 96 and also provides frictional engagement to retain adapter 33 on housing 31. A surface 97 on housing 31 spaced from suction inlet 92 includes a resilient catch 98 defining a latching mechanism. Catch 98 faces away from suction inlet 92 and is spaced a predetermined distance from suction inlet 92 such that it frictionally engages ridge 77 (FIG. 27) to retain adapter 33 on housing 31 when adapter 33 is attached to housing 31 (FIG. 5).

Housing 31 also includes a rear shell 100, a front shell 101 and an intermediate shell 102 that are mateably interconnected to form housing 31. Rear shell 100 defines an exterior surface 103 that includes contoured surfaces 91 and, in particular includes depressions 104 and raised surfaces 105 defining finger pads or rests for receiving the fingers of a mother using breast pump 30. Notably, depressions 104 and raised surfaces 105 define a "slip free" surface for receiving either a left hand or a right hand, thus facilitating use of breast pump 30 on either breast of the mother and by either hand of the mother, while requiring only one hand for operation. Inside of rear shell 100 are located ribs 106 for supporting suction unit 32 and further are additional ribs 107 for supporting batteries 107A in battery holder 95. Still further, rear shell 100 includes ribs 108' for supporting electrical contacts 109 for contacting the ends of the batteries.

Intermediate shell 102 includes a perimeter surface configured to mateably engage and nest in the concave structure of rear shell 100. Wall structure 128 at the top of intermediate shell 102 defines suction inlet 92. Rear shell 100 includes attachment bosses 113 and intermediate shell 102 includes mating holes and bosses for receiving screws 116 to retain intermediate shell 102 to rear shell 100. A rectangularly-shaped aperture 117 is formed in intermediate shell 102 and a battery access door or cover 118 is positioned to mateably cover aperture 117. Access door 118 includes tabs 119 and a resiliently supported latch 120 for engaging a notch 121 in the top of aperture 117. By releasing latch 120, access door 118 can be pivoted out of aperture 117 and batteries 107A can be placed within battery holder 95. Notably, the cross-sectional shape of the inner surface 122 and 123 on access door 118 and intermediate shell 102, respectively, define a concave, arcuate surface that extends about 90° around bottle 36 for protecting the bottle. Notably, the bottom surface 124 of rear shell 100 is generally planar and is located co-planar with the bottom 125 of bottle 36 (FIGS. 3-4) when bottle 36 is connected to breast pump 30. The center of gravity of breast pump 30 is located over the combined surface of 124 and 125 such that breast pump 30 can be rested stably in an upright position on a flat surface before or after its use, regardless of whether bottle 36 is full, partially full or empty. This not only makes it easier to use breast pump 30 since the breast pump 30 is not top heavy and does not tend to fall over when it is placed on a support surface, but further keeps check valve 82/83 cleaner. The location of the batteries 107A within battery holder 95 provides an optimal weight distribution which positions the center of gravity of the breast pump 30 generally below contoured surfaces 91 defining hand grip 90 such that breast pump 30 is convenient and comfortable to use, and such that breast pump 30 provides a balanced feel during use.

Front shell 101 (FIG. 5A) includes a U-shaped lower end 127 that fits around the structure 128 on intermediate shell 102 defining suction inlet 92. A pair of spaced apertures on both sides of suction inlet 92 align with mating bosses on intermediate shell 102 to receive screws for securing from shell 101 to intermediate shell 102. Lower end 127 also defines a generally rectangular opening 129 (FIGS. 2 and 3) receiving surface 88 of adapter 33 when the adapter is installed. Surface 88 closes opening 129 to continue the surface of lower housing end 127. The upper end of front shell 101 includes retaining tabs for engaging recesses in the upper end of rear shell 100 on both sides of switch 190. The upper half of front shell 101 includes a vertically extending slot 134 and a hole 135 spaced below slot 134. Both slot 134 and hole 135 are located at a thumb position 136 opposite the contoured surfaces 91 defining the hand grip. Thus, the controls located in slot 134 and hole 135 are easily accessible and useable by a mother while operating the breast pump 31 with only one hand. As shown in FIGS. 5 and 5A, hole 135 is covered by a pop-in-place, flexible, resilient plug 137 made of neutral or colored neoprene or the like.

Suction unit 32 is configured to be mateably positioned as a unit between rear shell 100 and front shell 101 in the upper section 90. Suction unit 32 (FIGS. 5, 5A, 6, and 14-19) includes a DC motor 140, a vacuum pump 141 operably connected to motor 140, and a mount 142 (FIG. 7) for supporting motor 140 and pump 141 within housing 31. Motor 140 is a 3V-DC electric motor. Vacuum or suction pump 141 includes a valve cover 143 and a valve bottom plate 144 defining a cavity 145 therebetween. A valve body 146 including a movable inlet valve 147 and a movable outlet valve 148 is positioned in cavity 145. A resilient, flexible pump piston or diaphragm 149 includes a lip 150 positioned between valve body 146 and valve bottom plate 144 and further includes a protrusion 151 connected to lip 150 by a flexible panel 152. Screws 159 hold valve cover 143 and plate 144 together. Protrusion 151 includes a hole 153. An offset driver 154 is engaged on the rotatable shaft 155 of motor 140. Offset driver 154 includes an offset finger 156 configured to engage hole 153 such that as DC motor shaft 155 rotates, finger 156 drives protrusion 151 reciprocatingly up and down within valve assembly 143/144/146. An inlet port 157 on valve cover 143 is operably connected to inlet valve 147. When pump 141 is operated, air is initially drawn from suction inlet 92 into vacuum inlet port 157 on valve cover 143 through an open inlet valve 147 and into cavity 145. As the valve body 146 reciprocatingly moves in an opposite direction, inlet valve 147 closes and the air is forced across cavity 145, through outlet valve 148, and out exhaust port 158.

Figure 19:
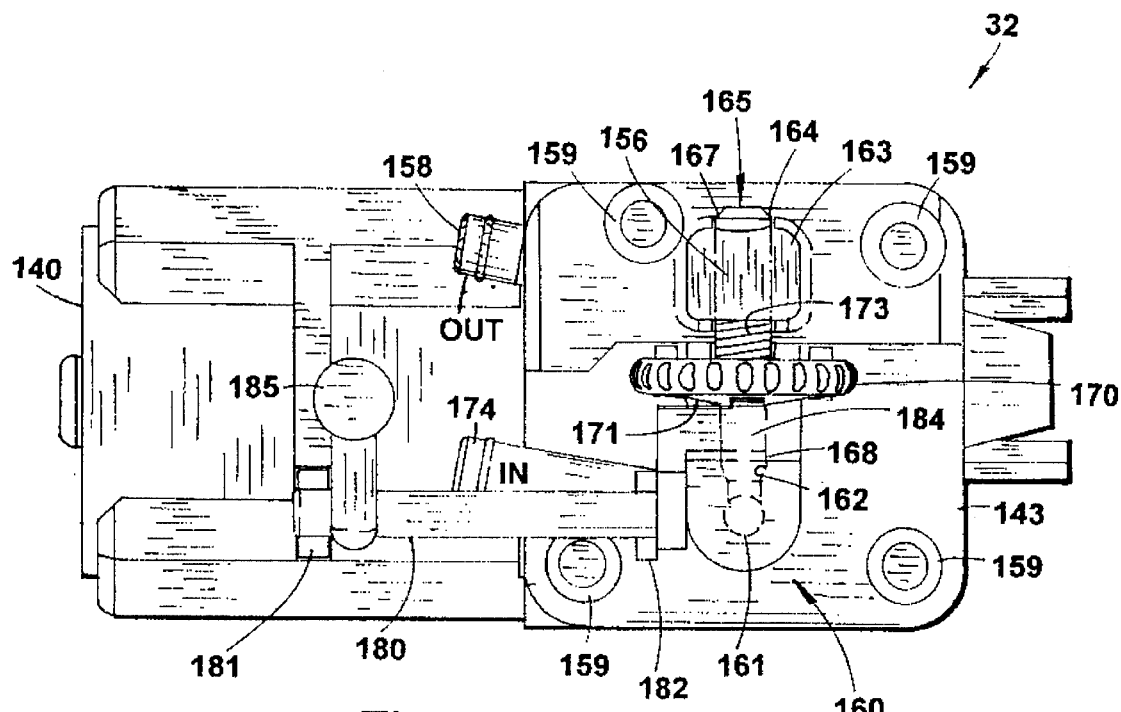
FIG. 19 is a plan view of the suction unit shown in FIG. 14.

A vacuum control valve 160 (FIG. 19) is positioned at vacuum inlet port 157. Vacuum control valve 160 includes an elbow-shaped passageway 161 including a valve seat 162. A structural protrusion 163 includes a hole 164 for supporting a rotatable vacuum control valve rod 165. Vacuum control valve rod 165 (FIGS. 20-22) includes a shaft 156 that includes a first end 167 rotatably supported in hole 164 (FIG. 19) and includes a second end 168 (FIG. 21) that is generally pointed for sealingly engaging valve seat 162 (FIG. 19). A thumb wheel 170 (FIG. 21) is positioned centrally on valve rod 165 and includes an inclined surface 171 defining a cam on one side. A spring 173 (FIG. 19) engaging the side of thumb wheel 170 biases valve rod second end 168 into sealing engagement with seat 162. A protrusion 172 (FIG. 14) extends upwardly from valve cover 143 and is positioned to engage inclined surface 171 as thumb wheel 170 is rotated such that valve rod 165 is gradually unseated from seat 162. Thus, the rotation of thumb wheel 170 allows fine adjustment of the vacuum generated at vacuum inlet port 157 by venting port 157 to atmosphere. A nipple 174 (FIG. 6) extends from vacuum port 157, and a tube 175 connects to nipple 174 and to a tubular protrusion 176 on the "back side" of suction inlet 92. An exhaust tube 177 extends from outlet valve 148 downwardly into lower section 93 generally adjacent and below the battery holder 95 for discharging air drawn from funnel 34 through stem 57 and vacuum pump 141. Tube 177 can also act as a drain for milk that finds its way into pump 141.

Figure 15:
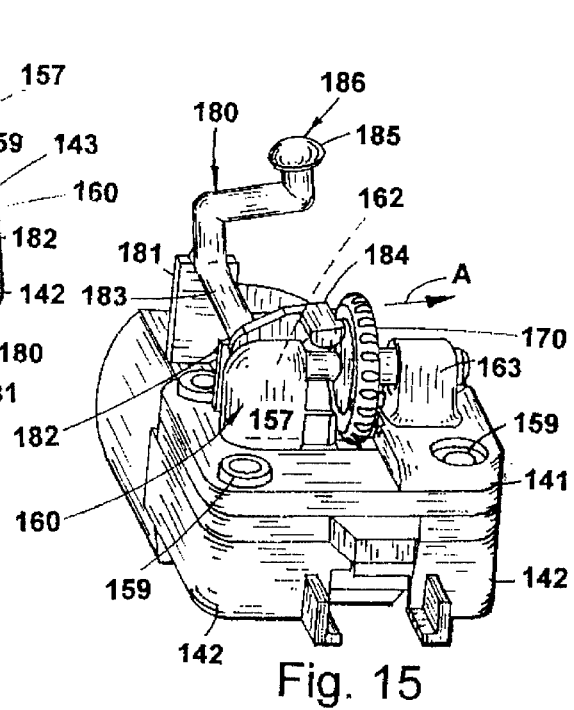
FIG. 15 is a top front perspective view of the suction unit shown in FIG. 14.
Figure 18:
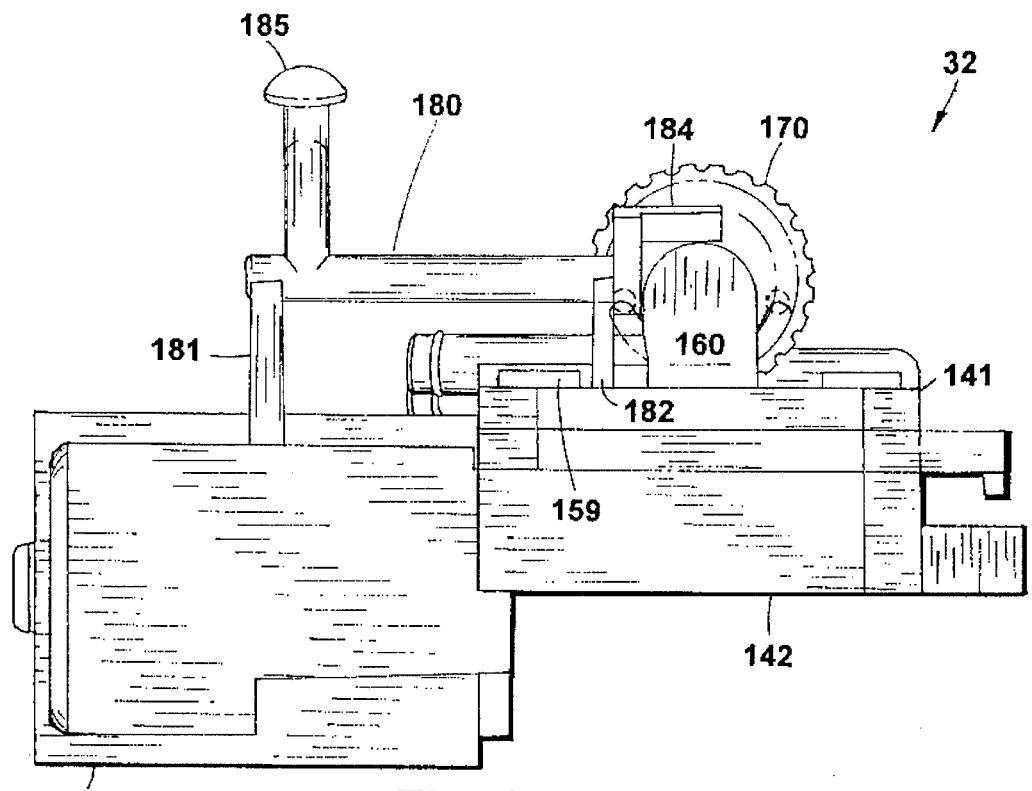
FIG. 18 is a side view of the suction unit shown in FIG. 14.

An articulated arm 180 (FIGS. 14-15) is rotationally supported on suction unit 32 by stanchions 181 and 182 and held onto stanchions by rib 182' on housing shell 101 (FIG. 5A). Rib 182' extends transverse to arm 180 and includes a "U" shaped end for mateably slideably engaging the shaft of arm 180. Alternatively, a finger bracket (not shown) can be extended from one of screws 159 around arm 180 to retain arm 180 on stanchions 181 and 182. Articulated arm 180 includes a shaft 183 rotatably engaging stanchions 181 and 182, a lever end 184, and an enlarged operating end 185. End 185 defines push button 186 which is located immediately below hole 135 in housing 31 and specifically is located underneath plug 137 on upper section 90 of front shell 101 (FIG. 5A). As push button 137/185/186 is depressed (FIG. 15), shaft 183 rotates and lever end 184 pivots into engagement with the side 187 of thumb wheel 170 (FIGS. 16, 17) causing rod 165 to move in direction "A" (FIG. 15). As valve rod 165 moves laterally, it opens valve 160. By repeatedly depressing push button 186, vacuum valve 160 produces a pulsing vacuum in funnel 34 for enhancing the extraction of milk as is desired by many mothers. By rotating thumb wheel 170, the vacuum at vacuum port 157 is controlled to a finely adjusted pressure.

A jack plug receptacle 138 (FIGS. 5 and 5A) is positioned behind a hole 139 at the bottom of rear shell 100 for receiving a jack extended from a AC/DC transformer. Jack plug receptacle 138 is electrically connected to the contacts 109 such that a mother can selectively use either batteries or an AC/DC transformer for supplying power to DC motor 140.

An on/off switch 190 (FIG. 5A) is located in an aperture 191 defined by notches in rear shell 100 and front shell 101 at the top of housing 31. Switch 190 is electrically connected to the electrical circuit 195, as discussed below.

The electrical circuit 195 (FIG. 13) of breast pump 30 for control of DC motor 140 includes a switch 190. Switch 190 includes an on/off slide 196 movably positioned in switch housing 197. Slide 196 is movable to a first position wherein contacts 198 and 199 are connected, and is movable to a second position wherein contacts 198 and 199 are disconnected. Contact 198 is connected by wire 200 to a positive terminal 201 of motor 140. Wire 202 extends from the second switch contact 199 to jack receptacle 203. A second wire 204 is operably connected to wire 202 at jack receptacle 203, and extends to battery positive contact 205. A wire 206 extends from negative battery contact 207 to the motor negative terminal 208. This establishes a circuit for running motor 140 by a battery 107A operably positioned on contacts 205 and 207. AC/DC transformer 209 includes wires 210 and 211 for operably connecting to an AC electrical power source 212 such as a household electrical wall outlet, and further includes wires 213 and 214 having a jack 215 on one end for communicating transformed DC current to jack, receptacle 203. Wire 216 is operably connected between jack receptacle 203 and negative battery contact 207 for communicating electrical current from wire 213 to terminal 207 when jack 215 is plugged into jack receptacle 203 and, thus to negative motor terminal 208. Wire 214 is also operably connected to wire 202 when jack 2 15 is plugged into jack receptacle 203. Thus, when jack 215 is plugged into jack receptacle 203, a circuit for running motor 140 by the AC/DC transformer 209 is established.

Notably, a variety of circuits are possible for operating motor 140. In the illustrated circuit 195, jack receptacle 203 is configured to disconnect wire 204 from wire 202 when jack 215 is plugged in. Thus, the batteries 107A are disconnected from the circuit for operating motor 140 when jack 215 is plugged into jack receptacle 203. Alternatively, it is contemplated that a circuit configured to recharge batteries 107A while also operating motor 140 can be constructed.

In operation, batteries 107A are placed in battery holder 95, or AC/DC transformer 209 is operably connected to the electrical circuit 195 of breast pump 30. Also, funnel 34, adapter 33, housing 31, and bottle 36 are interconnected to create a sealed system from the funnel 34 through the first passageway 63 of adapter 33 to bottle 36, and from bottle 36 through second passageway 70 of adapter 33 and suction inlet 92 to suction unit 32. As a mother grasps breast pump with her hand around the hand grip 91, her fingers securely engage depression 104 with her thumb positioned adjacent controls 170/185. The mother adjusts thumb wheel 170 with her thumb to finely control the amount of constant vacuum generated by suction unit 32, and/or repeatedly presses pulse button 185/186 with her thumb to create a pulsed vacuum. When switch 190 is moved to the "on" position, suction unit 32 withdraws air from suction inlet 92, causing a vacuum in bottle 36 and funnel 34. As milk begins to flow from the mother's breast 35, the milk flows through passageway 63 into bottle 36. If bottle 36 becomes full or if the breast pump 30 is turned onto its side, ball 82 is carried into sealing engagement against seal 83, thus substantially preventing milk from flowing into pump 141 and clogging the pump. Bottle 36 can be unscrewed from adapter 33, or adapter 33/bottle 36 can be pulled away as a unit from housing 31 for later separation. Adapter 33, funnel 34, and housing 31 can be readily separated for easy cleaning simply by pulling the components apart with a firm pull and/or a twisting pull.

In the foregoing description, it will be readily appreciated by those skilled in the art that modifications may be made to the invention without departing from the concepts disclosed herein. Such modifications are to be considered as included in the following claims, unless these claims expressly state otherwise.

The embodiments of the invention in which an exclusive property or privilege is claimed are defined as follows:

1. A breast pump comprising:

a housing;

a suction unit operably mounted to said housing, one of said housing and said suction unit defining a suction inlet;

an adapter including a tubular protrusion configured to engage said suction inlet and further including a funnel-supporting section for supporting a funnel to engage a mother's breast and a bottle-engaging section for holding a bottle to collect milk extracted from the mother's breast; and a pair of spaced "O" rings engaging said tubular protrusion and said suction inlet for creating a substantially air tight and stable seal between said tubular protrusion and said suction inlet and also creating friction to retain said adapter to said housing, said housing defining a hand grip and further defining a shroud located generally below said hand grip for partially protecting a bottle attached to said bottle-engaging section.

2. A breast pump as defined in claim 1 wherein said protrusion includes circumferential recesses for receiving said pair of "O" rings.

3. A breast pump as defined in claim 2 wherein said housing defines said suction inlet, and wherein said suction inlet defines a cylindrically-shaped surface configured to sealingly and frictionally engage said pair of "O" rings.

4. A breast pump as defined in claim 3 wherein said adapter includes a ball check valve located in said tubular protrusion.

5. A breast pump as defined in claim 4 wherein said pair of "O" rings and said valve are located on opposing sides of said bottle-engaging section.

6. A breast pump as defined in claim 1 wherein said suction unit includes a motor and a vacuum pump operably connected to said motor, and wherein said housing includes hardware for supplying current to said motor, said hardware including a battery holder for supplying DC power to said motor and a jack for receiving electrical current from an external power source for operating said motor.

7. A breast pump as defined in claim 1 wherein said adapter includes a check valve located in said tubular protrusion.

8. A breast pump as defined in claim 7 wherein said check valve includes an opening and a movable ball for sealingly engaging said opening to prevent back flow of milk through said tubular protrusion into the suction unit.

9. A breast pump as defined in claim 8 wherein said funnel-supporting section includes a first passageway and said tubular protrusion defines a second passageway, said first passageway being configured to communicate fluid and air from a funnel into a bottle connected to said adapter, said second passageway and said tubular protrusion communicating air from the bottle through said check valve to said suction unit.

10. A breast pump as defined in claim 1 wherein said housing includes an exterior contoured surface defining a hand grip with at least one shallow depression therein to receive a mother's finger to provide for slip-free handling of the breast pump.

11. A breast pump as defined in claim 1 wherein said shroud includes a space for receiving batteries for operating said motor, said space being located such that the center of gravity of the breast pump, when batteries are located in said battery holder, is below said hand grip.

12. A breast pump as defined in claim 1 wherein said housing defines a hand grip and includes first and second spaced apertures located on said hand grip, and including a suction control mechanism operably connected to said suction unit for controlling the suction generated by said suction unit, said suction control mechanism including a thumb wheel located in said first aperture for finely adjusting the vacuum in said suction unit and further including a thumb button for venting the suction unit to atmosphere for pulsing the vacuum.

13. A breast pump as defined in claim 1 including a detachable funnel for engaging a mother's breast.

14. A breast pump comprising:
   a housing;
   a suction unit operably mounted to said housing, one of said housing and said suction unit defining a suction inlet;
   an adapter including a tubular protrusion configured to engage said suction inlet and further including a funnel-supporting section for supporting a funnel to engage a mother's breast and a bottle-engaging section for holding a bottle to collect milk extracted from the mother's breast;
   a pair of spaced "O" rings engaging said tubular protrusion and said suction inlet for creating a substantially air tight and stable seal between said tubular protrusion and said suction inlet and also creating friction to retain said adapter to said housing, said housing defines a hand grip and further defines a shroud located generally below said hand grip for partially protecting a bottle attached to said bottle-engaging section; and
   a detachable funnel for engaging a mother's breast, said funnel including a frustoconical section having circumferentially extending undulations for engaging the mother's breast and further including a generally cylindrically-shaped section for engaging said funnel-supporting section.

15. A breast pump as defined in claim 1 wherein said funnel-supporting section includes a non-uniform surface spaced from said tubular protrusion and said housing defines a latching structure for engaging said non-uniform surface to frictionally secure said adapter to said housing.

16. A breast pump assembly, comprising:
   a breast pump having a suction inlet; and
   an adapter including:
   a cup-shaped section including a cylindrically-shaped side wall and a top wall configured to frictionally and sealingly engage a mouth of a bottle;
   a tubular protrusion extending from said top wall and defining a first passageway extending through said top wall, said tubular protrusion including a circumferentially extending recess;
   an "O" ring located in said circumferentially extending recess of said tubular protrusion for frictionally sealingly engaging the suction inlet on the breast pump, said "O" ring being spaced from said top wall such that said "O" ring stabilizes the adapter on the breast pump when engaged therewith;
   a check valve located in said first passageway of said tubular protrusion to prevent back flow of milk from the bottle through said first passageway;
   a funnel-supporting section connected to said cup-shaped section, said funnel-supporting section and said cup-shaped section defining a second passageway that extends through said top wall and that is spaced from said first passageway; and
   a second "O" ring spaced from said first "O" ring and located on said tubular protrusion for stabilizing the adapter on the breast pump, the first and second "O" rings and the suction inlet providing a connection structure that limits the engagement of the adapter and the breast pump to a linear movement, and further providing sufficient friction to securely but releasably hold the adapter to the breast pump during use.

17. A breast pump as defined in claim 16 wherein said check valve includes a movable ball and an opening adapted to be sealed by said ball to prevent back flow of milk through said first passageway.

18. A breast pump as defined in claim 16 wherein said tubular protrusion and said check valve are located on opposite sides of said top wall.

19. A breast pump as defined in claim 16 wherein said tubular protrusion and said funnel-supporting section include structure defining a latching mechanism therebetween for frictionally retaining said adapter to the breast pump.

20. A breast pump comprising:
   a funnel for mateably engaging a mother's breast;
   a suction unit for withdrawing air from said funnel to create a vacuum therein;
   a housing assembly configured to support said funnel and said suction unit, said housing assembly including a housing defining a hand grip having a thumb position located generally on the same side of the housing as the funnel; and
   controls located on said hand grip in said thumb position for controlling said suction unit.

21. A breast pump as defined in claim 20 wherein said controls are operably mounted in said housing and include a vacuum releasing pulse-type push button and a vacuum controlling fine adjustment mechanism, said push button and said fine adjustment mechanism being spaced from each other but being located on said thumb position in a readily accessible position for easy and comfortable activation by a mother, whereby the mother can operate the breast pump including adjusting and pulsing the vacuum with one hand while holding the breast pump.

22. A breast pump as defined in claim 21 wherein said fine adjustment mechanism includes a rotatable wheel operably engaged with said suction unit.

23. A breast pump as defined in claim 22 wherein said suction unit includes a valve for controlling the amount of vacuum generated by said suction unit, and wherein said push button and said rotatable wheel are operably connected to said valve for controlling the movement of said valve.

24. A breast pump as defined in claim 23 including an articulated arm connecting one of said push button and said rotatable wheel to said valve.

25. A hand held, portable breast pump comprising:
a vacuum-generating unit configured to mateably engage a mother's breast and to extract milk therefrom for collection in a container;
said vacuum generating unit including a housing and a suction unit operably mounted in the housing, said housing having contoured surfaces defining a hand grip with depressions shaped to mateably receive at least one finger of a mother's hand; and
a vacuum control mechanism located in said housing and operably connected to said suction unit including a valve for controlling the vacuum generated by said suction unit, a rotatable thumb wheel operably connected to said valve to control fine adjustment of the vacuum, and a push button operably connected to said valve and spaced from said thumb wheel for venting the suction unit to atmosphere to control the vacuum, said thumb wheel and said push button being operably mounted to said housing and being located on said hand grip for convenient operation by a thumb or a finger on the mother's hand while holding onto the hand grip, said thumb wheel and said push button being located on a same side of said hand grip and said thumb wheel being rotatable about an axis that is perpendicular to a line extending between the thumb wheel and the push button so that the mother's thumb or finger can be moved along the line to selectively operate the thumb wheel or push button.

26. A breast pump as defined in claim 25 wherein said contoured surfaces are configured to comfortably receive a mother's hand with the thumb of the mother's hand being naturally positioned proximate said thumb wheel and said push button.

27. A breast pump as defined in claim 25 wherein said valve comprises a rotatable shaft and said thumb wheel is attached to said shaft for rotating said shaft, said housing including a protrusion and said thumb wheel including a cam for engaging the protrusion to shift the shaft axially as said shaft is rotated.

28. A breast pump as defined in claim 25 including an articulated arm rotatably supported by said housing, said articulated arm including one end that defines said push button and another end that defines a lever for engaging and axially moving said valve.

29. A breast pump as defined in claim 28 wherein said lever engages a side of said thumb wheel.

30. A breast pump comprising:
a portable hand held vacuum-generating unit configured to mateably engage a mother's breast and to extract milk therefrom for collection in a bottle of predetermined size, said vacuum-generating unit including a bottle-engaging section and a shroud;
said shroud including a bottom surface spaced a predetermined distance from said bottle-engaging section such that said shroud bottom surface is generally coplanar with a bottom surface of the bottle when the bottle is engaged with said bottle-engaging section, whereby, when the bottle is assembled to the breast pump, said shroud bottom surface combines with the bottle bottom surface to stably support the breast pump and the bottle in an upright position.

31. A hand held, portable breast pump, comprising:
a housing including an upper section having a contoured surface defining a hand grip and a suction inlet, and further including a lower section defining a shroud having a concave generally arcuate surface for mateably partially surrounding and protecting a bottle;
a suction unit operably mounted in said housing and connected to said suction inlet;
a funnel configured to mateably engage a mother's breast; and
an adapter operably interconnecting said funnel and said housing, said adapter being configured to operably engage the bottle and position the bottle in a protected position adjacent the arcuate surface of the shroud.

32. A breast pump as defined in claim 31 wherein said contoured surface defining said hand grip includes a short, circumferentially extending depression for receiving a mother's finger.

33. A breast pump as defined in claim 31 wherein said lower section defines a battery holder.

34. A breast pump as defined in claim 31 wherein said housing is configured to position the center of gravity of the breast pump below said hand grip for improved balance when batteries are placed in said battery holder.

35. A breast pump as defined in claim 34 wherein said lower section includes a jack for receiving electrical current from an AC/DC transformer.

36. A breast pump as defined in claim 31 wherein said housing includes a jack for receiving current from an AC/DC transformer.

37. A breast pump as defined in claim 31 wherein said shroud is configured to extend about 90° around the bottle.

38. A breast pump as defined in claim 31 including a vacuum control mechanism for controlling said suction unit, said vacuum control mechanism including vacuum controls positioned at a thumb position on said hand grip.

39. A breast pump as defined in claim 38 wherein said vacuum controls include a rotatable adjustment wheel for fine vacuum adjustment and a push button for venting the suction unit to atmosphere to create a pulsing effect.

40. A self-supporting funnel for a breast pump comprising:
a generally cylindrically-shaped tubular section comprising resilient material, said tubular section having a constant wall thickness and configured to mateably engage a breast pump for delivering milk to a container attached to the breast pump; and
a generally frustoconically-shaped funnel section for mateably engaging a mother's breast, said funnel section comprising resilient material defining a constant thickness wall with at least three circumferentially extending ring-shaped undulations that cause said wall to flex in a symmetrical manner to comfortably and sealingly engage a mother's breast despite physical differences in size and shape of breasts from one mother to another.

41. A self-supporting funnel as defined in claim 40 wherein the undulations of said frustoconically-shaped funnel section each have a substantially identical cross-sectional shape.

42. A self-supporting funnel as defined in claim 41 wherein said funnel section defines a longitudinally extending axis and a plurality of tangential lines each of which extend through said axis at an angle to said axis and that tangentially contact the interior surface of said funnel section in at least three locations.

43. A self-supporting funnel as defined in claim 40 wherein the depth of said undulations is about equal to the thickness of said constant thickness wall.

* * * * *